(12) United States Patent
Schmidt et al.

(10) Patent No.: US 8,206,333 B2
(45) Date of Patent: Jun. 26, 2012

(54) OCULAR IMPLANT

(75) Inventors: Wolfram Schmidt, Rostock (DE);
Katrin Sternberg, Rostock (DE); Detlef Behrend, Rostock (DE); Rudolf Guthoff, Rostock (DE); Klaus-Peter Schmitz, Rostock (DE)

(73) Assignee: Universitaet Rostock, Rostock (DE)

( * ) Notice: Subject to any disclaimer, the term of this patent is extended or adjusted under 35 U.S.C. 154(b) by 374 days.

(21) Appl. No.: 12/524,719

(22) PCT Filed: Jan. 25, 2008

(86) PCT No.: PCT/EP2008/050903
§ 371 (c)(1),
(2), (4) Date: Aug. 24, 2009

(87) PCT Pub. No.: WO2008/090225
PCT Pub. Date: Jul. 31, 2008

(65) Prior Publication Data
US 2009/0326432 A1    Dec. 31, 2009

(30) Foreign Application Priority Data

Jan. 25, 2007 (DE) .......................... 10 2007 004 906

(51) Int. Cl.
*A61M 5/00* (2006.01)
(52) U.S. Cl. .................. 604/9; 604/5.04; 604/8; 604/10; 604/19; 604/27; 604/28; 604/48; 604/93.01; 604/540; 604/541; 604/284; 604/285; 604/286; 604/288; 604/289; 604/290; 427/2.1; 427/2.24; 427/2.25; 600/398; 600/399

(58) Field of Classification Search ............... 604/5.04, 604/8–10
See application file for complete search history.

(56) References Cited

U.S. PATENT DOCUMENTS
5,041,081 A    8/1991    Odrich
(Continued)

FOREIGN PATENT DOCUMENTS
WO    WO 03/099175    * 12/2003

OTHER PUBLICATIONS

International Search Report for International Application No. PCT/EP2008/050903 dated Jun. 5, 2008.

*Primary Examiner* — Tatyana Zalukaeva
*Assistant Examiner* — Ilya Treyger
(74) *Attorney, Agent, or Firm* — Pearl Cohen Zedek Latzer, LLP

(57) ABSTRACT

The present invention relates to an ocular implant, particularly a glaucoma stent.
It is the object of the present invention to devise an ocular implant which allows the ocular eye pressure to be regulated, i.e., to be maintained at a desired level, while preventing the flow resistance from increasing over time, for example due to fibrosis.
In order to achieve this object, the ocular implant according to the invention comprises a small tube (5), the wall surface (3) of which encloses a hollow duct that is open on both sides in the longitudinal direction of the hollow duct, wherein a first opening (1) allowing ocular humor to flow in and a second opening (2) allowing the ocular humor to be discharged is provided, and wherein the wall surface (3) is formed by a liquid-tight material, and wherein at least one pressure-controlled valve (4) is disposed in the area of the wall surface (3).

18 Claims, 4 Drawing Sheets

U.S. PATENT DOCUMENTS

Figure 1:
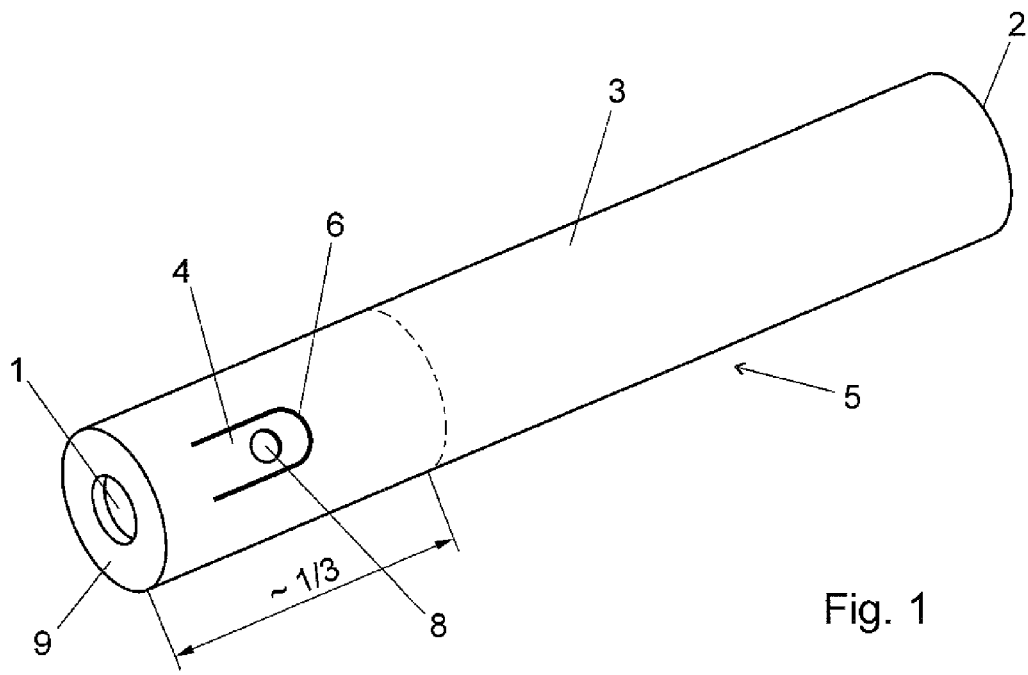

| | | |
|---|---|---|
| 5,127,901 A | 7/1992 | Odrich |
| 5,338,291 A * | 8/1994 | Speckman et al. ............... 604/9 |
| 6,508,779 B1 * | 1/2003 | Suson ............................. 604/8 |
| 6,730,056 B1 | 5/2004 | Ghaem et al. |
| 7,025,740 B2 | 4/2006 | Ahmed |
| 2003/0135149 A1 * | 7/2003 | Cullen et al. ..................... 604/9 |
| 2005/0125003 A1 | 6/2005 | Pinchuk et al. |

* cited by examiner

Schnitt X-X

OCULAR IMPLANT

CROSS-REFERENCE TO RELATED APPLICATIONS

This application is a National Phase Application of PCT International Application No. PCT/EP2008/050903, International Filing Date Jan. 25, 2008, claiming priority of German Patent Application, 10 2007 004 906.6, filed Jan. 25, 2007, which is hereby incorporated by reference.

The present invention relates to an ocular implant, particularly a glaucoma stent having the features set forth in claim 1.

The present invention belongs to the field of medical technology and is an improvement of an existing method of treatment of glaucoma. The term glaucoma, colloquially also termed "Gruener Star", describes a group of ophthalmic diseases characterized by a temporarily or permanently increased intraocular pressure which obstructs the blood supply of the optic nerve. In case of a long-term insufficient supply of blood, the optic nerve is damaged and may die in extreme cases. The glaucoma is a major cause of blindness, particularly because it often goes unidentified and thus untreated for too long due to its course of disease frequently not showing any symptoms. It is assumed that in addition to the officially registered patients (about a million) just as many persons again are affected by this disease in Germany. About 10% of them are threatened by blindness.

Glaucoma are mainly divided into the categories of primary and secondary glaucoma, the latter occurring rather as epiphenomena of other diseases, respectively, according to anatomic characteristics, into closed-angle glaucoma and open-angle glaucoma. These terms refer to the angle between the posterior surface of the cornea and the anterior surface of the iris. All glaucoma have in common that ocular humor, a specific fluid supplying nutrients to the iris and the cornea while evacuating metabolic end products, cannot be sufficiently discharged due to several reasons. Since the ocular humor is constantly reproduced the prevented drainage results in an increase of pressure in the closed system that is the eye.

The so-called primary open-angle glaucoma is the most frequent type of glaucoma (circa 80-90%). In primary open-angle glaucoma the drainage is prevented directly in the drainage area of the chamber angle, the so called trabecular meshwork. The trabecular meshwork, a filter system positioned in the angle between the cornea and the iris (chamber angle), consists of fine pores. Since their dimensions are reduced for so far unknown reasons, the ocular humor cannot be discharged via the trabecular meshwork, and further on via the so called Schlemm's canal, into the episcleral veins as in a healthy eye.

Firstly, the therapy of glaucoma is classified into medicinal therapies, laser treatments and surgical methods. The latter, in which category falls the present invention, are not employed until the two first methods have failed, and aim to surgically create a drainage possibility for the ocular humor. In open-angle glaucoma this aim is generally achieved by a trabeculectomy in which a duct is created allowing the ocular humor to be discharged from the anterior chamber under the conjunctiva into a so-called trickling bleb (also called filtering bleb). Since there are wounds and the created opening may naturally close again as a result of fibrosis (development of excess collagen fibres/excess fibrous connective tissue), such a surgery often is not permanently successful. In case of a failed trabeculectomy, or in the USA even before, alloplastic implants, so-called drainage systems, respectively, drainage implants (stents), are used.

Typically, glaucoma implants consist of a silicone elastomer tube that transports the ocular humor out of the inner eye to lead it to a drainage plate of diverse material. A connective tissue structure of varying thickness develops around the drainage plate, through which ocular humor diffuses into the surroundings. Depending on the initial situation and the wound healing reaction, it is possible to control the intraocular pressure by implants in 50-100% of the cases for many years. However, problems arise in the implantation of a drainage system because hypotension (too low intraocular pressure) may occur as a result of the uncontrolled drainage of the ocular humor and may result in choroidal detachment to the point of bleeding as well as in corneal decompensation due to a collapsed anterior chamber. The cross section of the stents is adapted to the pressure conditions at the time of the implantation in order to regulate the drainage. Generally, the flow resistance rises when fibrosis begins in connection with the wound healing process, so that the initially desired flow rate may decrease and the intended balance may be disturbed again. Until today, a new medical intervention is required in these cases.

To prevent complications due to hypotension, implants (U.S. Pat. No. 5,041,081; U.S. Pat. No. 7,025,740 B2 and U.S. Pat. No. 5,127,901) having a valve mechanism which is to limit the drainage of ocular humor are known in the art. These are exclusively check valve mechanisms automatically locking the passage of the ocular humor in a flow direction. If the intraocular pressure is too high, the valve opens, that means, it offers a certain resistance compared to an uncontrolled drainage. Principally, however, this mechanism can only prevent the reflux of the ocular humor, which in normal circumstances is physically excluded. For that, the pressure at the outside would have to exceed the pressure inside the eye, like e.g. in case of deep sea diving. The aforementioned solutions do not provide any protection from the flow resistance increasing over time, for example due to fibrosis.

Accordingly, the object of the present invention is to devise an ocular implant (glaucoma stent) which allows the ocular eye pressure to be regulated, i.e., to be maintained at a desired level, while preventing the flow resistance from increasing over time, for example due to fibrosis.

This object is achieved according to the invention by the features of the characterizing portion of claim 1 in conjunction with the features set forth in the preamble. Preferred embodiments of the invention are contained in the subclaims.

The glaucoma stent according to the invention comprises pressure-controlled valves which are opened by an increased intraocular pressure and which are shut when the pressure decreases again, those pressure-controlled valves being disposed in the stent wall (and not inside the stent). This allows for the drainage to be regulated and for a constantly optimally adjusted flow rate to be achieved, because the pressure-controlled valves disposed in the stent wall additionally allow the ocular humor collected at the exterior walls of the stent to be discharged. The drainage can be assured even in case of gradual stenosis of the stent, because a new possibility for ocular humor to flow in is provided, which discharges ocular humor only in case of an accordingly high intraocular pressure. Thus, a solution for ensuring an optimally adjusted drainage of ocular humor and for achieving a constant intraocular pressure in case of altered intraocular pressure (compared to the implantation time) as well as in case of increased flow resistance is provided.

For this purpose, the ocular implant according to the invention comprises a small tube, the wall surface of which encloses a hollow duct that is open on both sides in the longitudinal direction of the hollow duct, wherein a first opening allowing ocular humor to flow in and a second opening allowing the ocular humor to be discharged is provided, and wherein the wall surface is formed by a liquid-tight material, and wherein at least one pressure-controlled valve is disposed in the area of the wall surface.

Preferably, the at least one pressure-controlled valve is disposed in the area of the wall surface, but not in the area of the first opening (allowing the ocular humor to flow in), i.e., not in the edge portion of the wall surface (forming the first opening, respectively, being adjacent to the first opening). Thereby, at least one further opening allowing ocular humor to flow in, which opens not until a specific pressure is reached, is provided adjacent to the first opening allowing ocular humor to flow in.

Preferably, the wall material, the wall thickness and the wall thickness distribution over the length of the small tube are selected such that the small tube, after being inserted into the anterior chamber of the eye, remains placed therein in such a way that the first opening is positioned in the anterior eye chamber and that the second opening is positioned in the subconjunctival space. It is also preferred that the wall material, the wall thickness and the wall thickness distribution over the length of the small tube are selected such that the small tube, after being inserted into the anterior chamber of the eye, remains placed therein in such a way that the first opening is positioned in the anterior eye chamber and that the second opening is positioned in the uveoscleral space.

Preferably, the internal hollow duct of the small tube has a diameter of between 50 µm and 1000 µm. Preferably, the hollow duct has a minimum inside diameter of between 50 µm and 80 µm along its longitudinal direction. Preferably, the hollow duct has a maximum inside diameter of between 300 µm and 1000 µm, and more preferably of between 350 µm and 400 µm, along its longitudinal direction. Preferably, the hollow duct comprises a flow limiter formed by an orifice, wherein the orifice comprises an opening the area of which is between 1000 and 3000 µm$^2$, and more preferably between 1500 and 2000 µm$^2$. Preferably, the orifice comprises a circular opening having a diameter of between 35 µm and 60 µm, and more preferably of between 40 µm and 50 µm. Preferably, the orifice is disposed at a distance from the first opening corresponding to between 0% and 10% of the longitudinal extent of the small tube. More preferably, the orifice is disposed directly at the first opening. Due to the preferred dimensions of the diameter of the small tube and the orifice, it is possible to adjust the drainage of the stent according to the invention in such a way that the intraocular pressure can be regulated. It is possible to select the diameter of the small tube large enough that there is no increase of the flow resistance inside the hollow duct, e.g. due to fibrosis. Although the flow resistance may increase in the area of the orifice (the diameter of which is considerably smaller)—e.g. due to fibrosis—, a new, additional possibility for the ocular humor to flow in is provided by the pressure-controlled valves disposed in the side wall of the small tube, which are able to compensate the clogging of the flow limiter (orifice), e.g. due to fibrosis.

Preferably, the small tube has a length of between 3 mm and 20 mm. Preferably, the small tube has a wall thickness of between 10 µm and 200 µm. Preferably, the small tube has a minimum wall thickness of between 10 µm and 20 µm along its longitudinal direction. Preferably, the small tube has a maximum wall thickness of between 80 µm and 100 µm along its longitudinal direction. Preferably, the hollow duct of the small tube extends over the entire length between the two ends of the small tube.

Preferably, the first opening is disposed directly at the first end of the small tube, and the second opening is disposed directly at the second end of the small tube. Preferably, the small tube has a homogenous wall thickness. Preferably, the small tube forms a straight hollow cylinder or an oblique hollow cylinder. Preferably, the small tube is formed of a flexible material, a metal or a metal alloy. Preferably, the wall surface of the small tube is formed of a flexible material, preferably an elastomer. Alternatively, the wall surface of the small tube is formed of a metal or a metal alloy. More preferably, the wall surface of the small tube is formed of a shape memory alloy (NiTi) or of the stainless steel 316L.

Preferably, the first opening and/or the second opening are formed in a ring-shape. Preferably, the valve is formed as a diaphragm valve/tongue diaphragm valve, and more preferably as a tongue diaphragm valve. Preferably, the diaphragm valve is formed by a base and a circumferential separation of the wall surface, wherein the wall surface is not separated in the area of the base. Preferably, the wall thickness of the wall surface is smaller in the area of the base than the wall thickness of the wall surface in the adjacent area outside the valve. Preferably, the wall thickness of the wall surface in the area of the base is between 30 and 80% of the wall thickness of the wall surface in the adjacent area outside the valve. A reduced wall thickness of the wall surface allows the valve to be opened easily in case of increased intraocular pressure. At this, the wall thickness of the wall surface is dimensioned such that the pressure-controlled valve begins to open as soon as a pressure of 10 mm mercury column is reached, that it is completely opened as soon as a pressure of 20 mm mercury column is reached, and that it opens continuously at a pressure of between 10 mm and 20 mm mercury column.

Preferably, the circumferential separation is formed by a gap in the wall surface of the small tube, wherein the gap has a width of between 2 µm and 20 µm. Preferably, the diaphragm of the diaphragm valve or the diaphragm of the tongue diaphragm valve comprises at least one opening, wherein the opening (8) has an area of between 500 and 2000 µm$^2$. Even in the closed state of the valve this opening allows a minimum flow preventing the valve from closing again.

Preferably, the base of the valve is directed to the first opening while the circumferential separation is directed from the base in the direction of the second opening. Preferably, the valve comprises an area corresponding to between 5% and 10% of the area of the wall surface of the small tube. Preferably, the valve has a longitudinal axis extent along the longitudinal axis of the small tube that does not exceed 15% of the length of the small tube, and a radial transverse extent that does not exceed 15% of the circumference of the small tube.

Preferably, a plurality of (circumferentially disposed) valves are provided. Preferably, 2 to 8 valves are provided. Preferably, in the radial direction, a maximum of 4 valves are adjacently offset in the longitudinal direction, and a maximum of 2 valves are disposed one behind the other in the axial direction. Preferably, the valves together have an area corresponding to between 10% and 35% of the area of the wall surface of the small tube. Disposing multiple valves allows for the creation of a largest possible additional drainage region with sufficient strength of the stents. Additionally, the valves are dimensioned such that they have a high reliability.

Preferably, the stent is positioned up to 35% of its length in the anterior eye chamber. Preferably, the valves are disposed at a distance from the first opening equal to between 0% and 35% of the longitudinal extent of the small tube. Preferably, the valves are disposed at a distance from the first opening equal to between 5% and 35% of the longitudinal extent of the small tube. Accordingly, it is preferably proposed that no valves are provided on the lateral surface at a distance from the first opening equal to between 35% and 100% of the longitudinal extent of the small tube.

Figure 2:
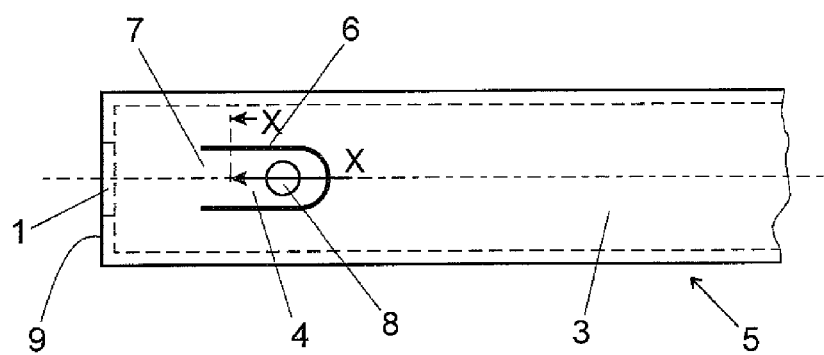
Figure 3:
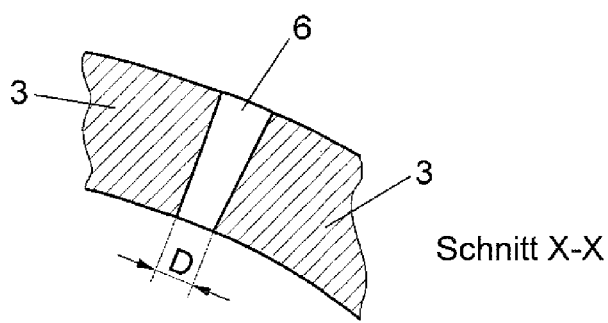
Figure 4:
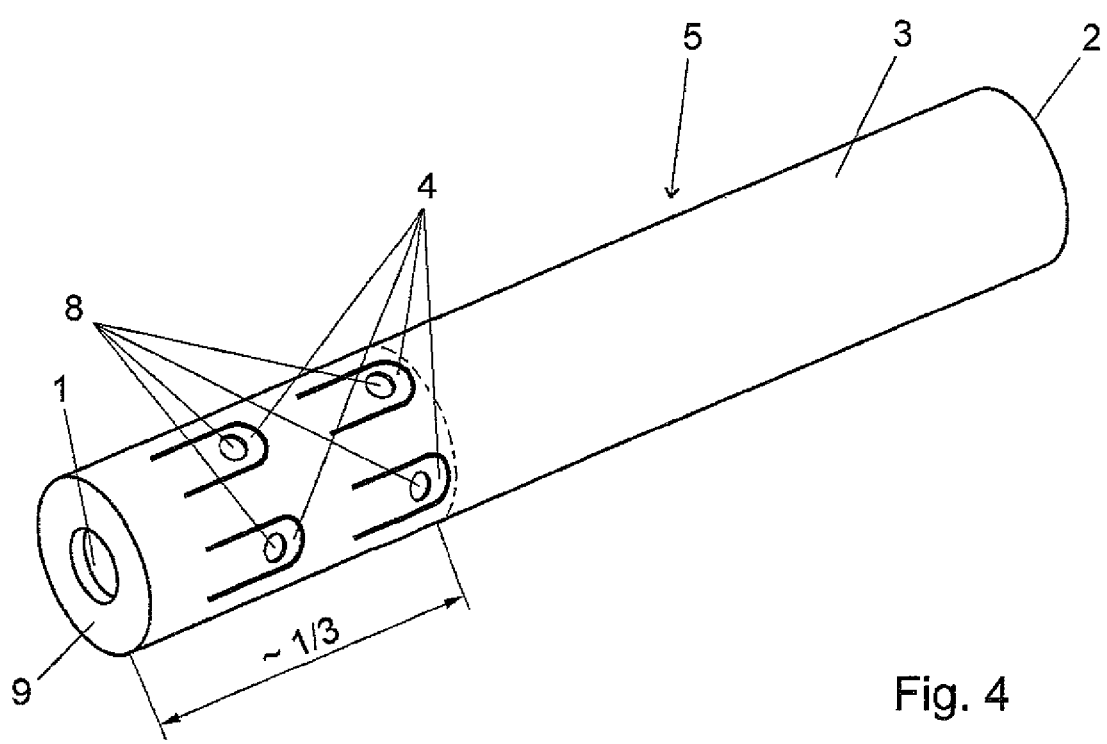
Figure 5A:
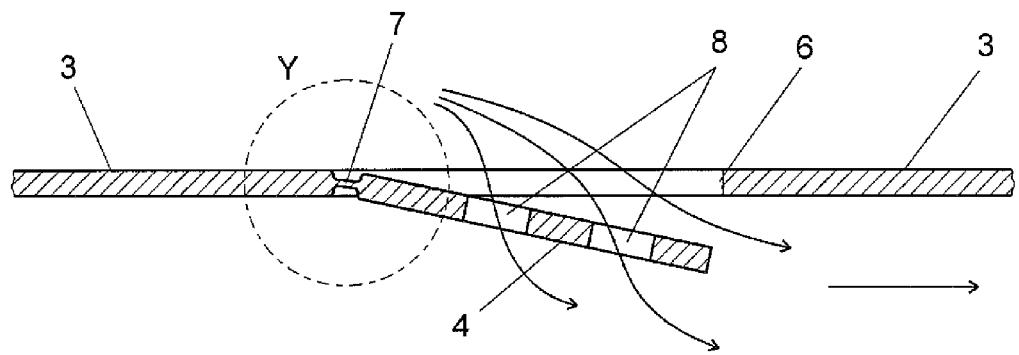
Figure 5B:
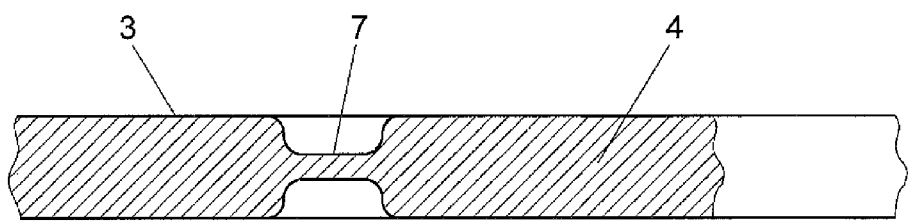
Figure 5C:
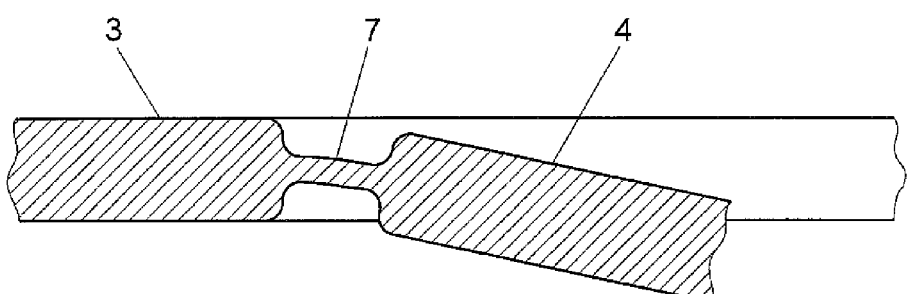
Figure 6A:
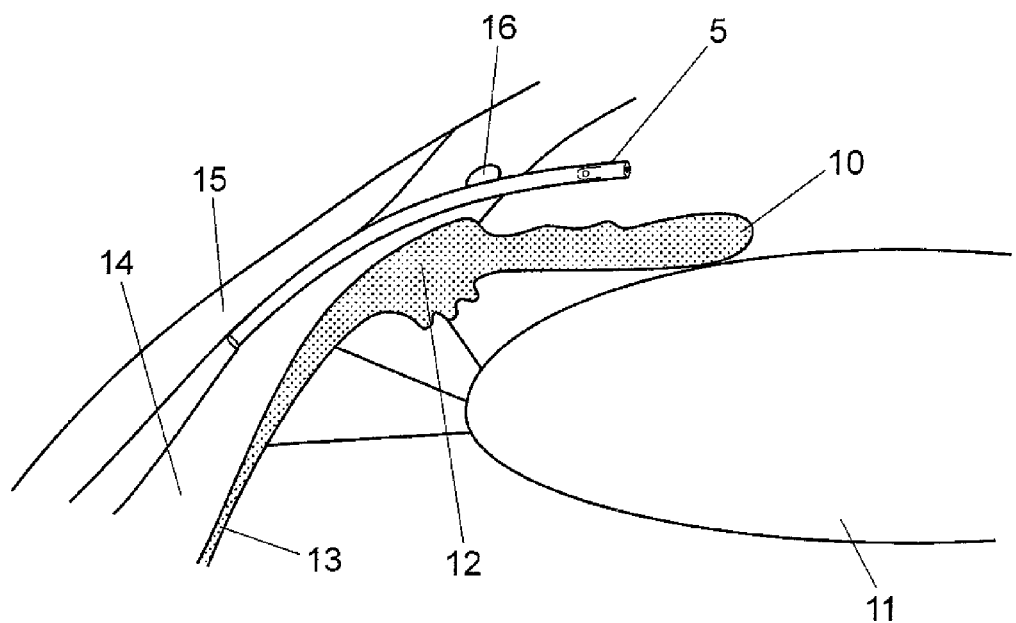
Figure 6B:
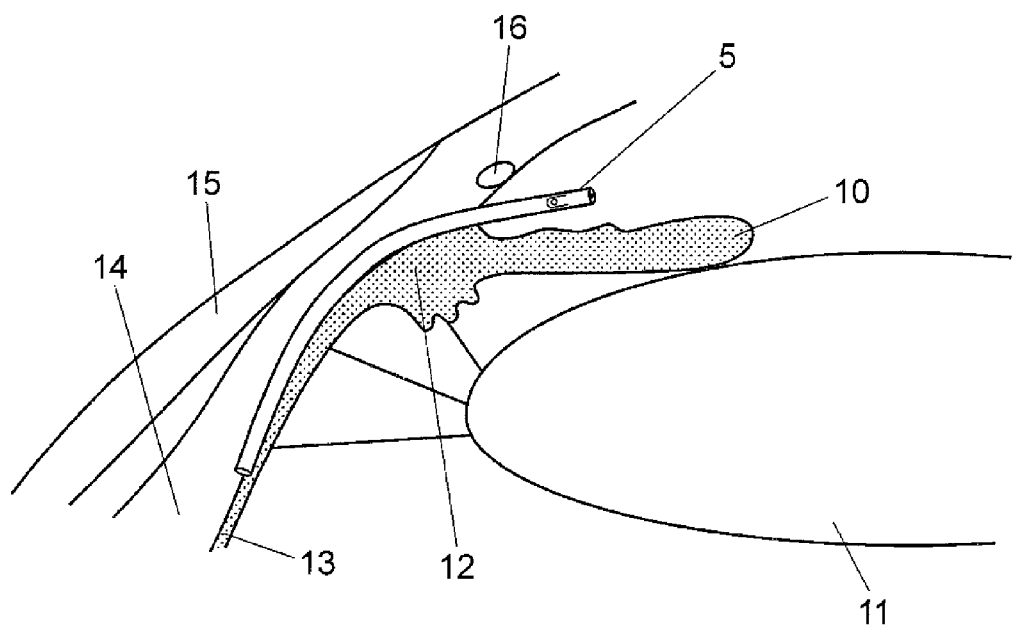

The invention will be described hereinafter in more detail with reference to embodiments illustrated in the figures. In the drawings:

FIG. 1 shows an ocular implant according to the invention in a perspective view, FIG. 2 shows an ocular implant according to the invention in a top view, FIG. 3 is a sectional view of the ocular implant shown in FIG. 2 as taken on line X-X', FIG. 4 shows an ocular implant according to the invention having a plurality of pressure-controlled valves in a perspective view, FIG. 5a) shows a pressure-controlled valve (in a half-open position) disposed in the wall surface of the stent in a schematic sectional view, FIG. 5b) is an enhanced view of the area Y marked in FIG. 5a, wherein the pressure-controlled valve is in a closed state, FIG. 5c) is an enhanced view of the area Y marked in FIG. 5a, wherein the pressure-controlled valve is in an opened state, FIG. 6a) is a schematic view of the preferred positioning of the ocular implant according to the invention allowing drainage of the ocular humor into the subconjunctival space, and FIG. 6b) is a schematic view of the preferred positioning of the ocular implant according to the invention allowing drainage of the ocular humor into the uveoscleral space.

FIG. 1 shows a stent (ocular implant) according to the invention in a perspective view. The stent consists of a small tube 5 preferably having an inside diameter of 350 to 400 μm. This inside diameter is dimensioned such that the flow resistance of the hollow duct formed in the small tube 5 does not vary substantially, because phenomena like e.g. fibrosis or the like that may cause openings to clog show no, respectively, negligible effects with such a large inside diameter. The hollow duct formed by the small tube 5 comprises a first opening 1 and a second opening 2. The stent 5 will afterwards be placed in the eye in such a way that the first opening 1 will be positioned in the anterior eye chamber and that the second opening 2 will be positioned outside the anterior eye chamber, for example in the subconjunctival space or in the uveoscleral space. At this, it is preferably proposed that, approximately one-third of the length of the stent 5 measured from the first opening 1 is positioned in the anterior eye chamber (along its longitudinal axis). Furthermore, it is proposed according to the invention that a flow limiter preferably formed as orifice 9 and disposed directly at the first opening 1 is provided. The diameter of the orifice 9 is dimensioned according to the patient's intraocular pressure and preferably ranges between 30 and 70 μm. This diameter has to be dimensioned such that hypotension of the eye likely to provoke a collapse of the anterior eye chamber is definitely excluded.

According to the invention, at least one pressure-controlled valve 4 is positioned on the wall surface (lateral surface) 3 of the stent 5, which continually opens as soon as an intraocular pressure of preferably 10 mm mercury column is reached (up to an intraocular pressure of preferably 20 mm mercury column). Such a pressure-controlled valve 4 creates an additional possibility for the ocular humor to flow into the stent 5 and thus an additional possibility for the ocular humor to be discharged in case of increased pressure, even if the flow resistance through the orifice 9 increases over the time, e.g. due to fibrosis. Thus, it is possible to ensure a long-term pressure regulation, so that the stent 5 according to the invention can remain longer in a patient's eye than conventional stents in accordance with the state of the art. This makes it possible to prevent additional surgeries for changing a stent.

FIG. 2 shows the stent illustrated in FIG. 1 in a plan view. Preferably, the pressure-controlled valve 4 is configured as a tongue diaphragm valve. Such a tongue diaphragm valve 4 comprises a base 7 and a circumferential separation 6 of the wall surface 3. The circumferential separation 6 allows the pressure-controlled valve 4 to move inwards (in the direction of the hollow duct) in case of increased ocular humor pressure so that an additional possibility for the ocular humor to flow in is created. Preferably, the pressure-controlled valve 4 may be formed as tongue diaphragm valve, though its configuration is not limited thereto. Thereby, it is preferably proposed that a partially circumferential separation allows the valve to open in case of increased intraocular pressure (preferably as soon as the pressure reaches 10 mm mercury column).

FIG. 3 shows an enhanced sectional view of the ocular implant illustrated in FIG. 2 as taken on line X-X'. As is apparent from the figure, the (partially) circumferential separation 6 is formed by a gap in the wall surface 3. Preferably, this gap has a gap width D of between 10 and 20 μm. With such a gap width the gap itself has no flow function, i.e., the ocular humor itself cannot be discharged through the gap if the pressure-controlled valve 4 is not opened by bending in the direction of the hollow duct. The gap ensures the free movement of the valve tongue. In a preferred embodiment, the gap has a tapered form.

FIG. 4 shows a stent according to the invention in a perspective view comprising a plurality of pressure-controlled valves 4. In order to maintain the additional possible inflow area of the stent inside the anterior eye chamber as large as possible while ensuring a maximum and sufficient stability of the entire stent, preferably a plurality of pressure-controlled valves 4 that do not cover more than 30% of the total lateral surface of the stent are provided. In a particularly preferred embodiment, respectively four valves are provided circumferentially offset in two rows one behind the other (along the longitudinal axis of the stent), respectively.

FIG. 5a) shows a pressure-controlled valve 4 according to the invention in a schematic sectional view. The pressure-controlled valve 4 is formed by a partially circumferential separation 6 of the wall surface 3, which is provided in the wall surface 3. Merely in the area of the base 7 of the pressure-controlled tongue diaphragm valve 4 the wall surface 3 is not completely separated. FIG. 5c) shows the pressure-controlled valve 4 according to the invention in an opened state, the corresponding pressure-controlled valve 4 of FIG. 5b) being illustrated schematically in the closed state. As appears from the FIGS. 5b) and c), the thickness of the wall surface 3 is reduced in the area of the base 7 to allow the pressure-controlled valve 4 to be elastically opened in a simple manner in the direction of the hollow duct in case of an increased intraocular pressure in the anterior eye chamber.

As appears from the FIGS. 1, 2, 4 and 5a), the pressure-controlled valves 4 may comprise additional openings 8 in the area of their diaphragm (tongue) allowing for another (permanent) drainage of the ocular humor.

FIGS. 6a) and 6b) show by way of example a possible placement of the ocular implant with the opening 1 positioned in the anterior eye chamber and the opening 2 positioned in the subconjunctival space (FIG. 6a) or in the uveoscleral space (FIG. 6b).

List of Reference Numberals
1 first opening
2 second opening
3 wall surface
4 pressure-controlled valve 5 small tube/ocular implant
6 circumferential separation of the wall surface/gap
7 tongue base/tongue bone
8 opening in the valve
9 orifice
10 iris
11 lens
12 ciliary body
13 choroid
14 sclera
15 conjunctiva
16 trabecular meshwork/Schlemm's canal The invention claimed:

1. An ocular implant, comprising:
a small tube, the wall surface of which encloses a hollow duct that is open on both sides in the longitudinal direction of the hollow duct, wherein a first opening allowing ocular humor to flow in and a second opening allowing the ocular humor to be discharged is provided, and wherein the wall surface is formed by a liquid-tight material;
wherein 35% of the longitudinal extent of the small tube from the first opening is positioned in the anterior eye chamber; and
wherein at least one pressure-controlled valve is disposed in the area of the wall surface which is disposed at distance from the first opening equal to between 0% and 35% of the longitudinal extent of the small tube; and
wherein the valve is formed as a diaphragm valve or as a tongue diaphragm valve, wherein the diaphragm valve is formed by a base and a circumferential separation of the wall surface and wherein the tongue diaphragm valve is formed by a base and a tongue-shaped circumferential separation of the wall surface, wherein the wall surface is not separated in the area of the base.

2. The ocular implant according to claim 1, wherein the wall material and the wall thickness of the small tube are selected such that the small tube, after being inserted into the anterior chamber of the eye, remains placed therein in such a way that the second opening is positioned in the subconjunctival space or in the uveoscleral space.

3. The ocular implant according to claim 1, wherein the internal hollow duct of the small tube has a diameter of between 50 μm and 1000 μ.

4. The ocular implant according to claim 1, wherein the small tube has a length of between 3 mm and 20 mm.

5. The ocular implant according to claim 1, wherein the wall surface of the small tube is formed of a flexible material, a metal or a metal alloy.

6. The ocular implant according to claim 1, wherein the wall thickness of the wall surface is smaller in the area of the base than the wall thickness of the wall surface in the adjacent area outside the valve.

7. The ocular implant according to claim 6, wherein the wall thickness of the wall surface in the area of the base is between 30% and 80% of the wall thickness of the wall surface in the adjacent area outside the valve.

8. The ocular implant according to claim 1, wherein the base of the valve is directed to the first opening and the circumferential separation or the tongue-shaped circumferential separation is directed from the base in the direction of the second opening.

9. The ocular implant according to claim 1, wherein the valve has an area corresponding to between 5% and 10% of the area of the wall surface of the small tube.

10. The ocular implant according to claim 1, wherein the valve has a longitudinal axis extent along the longitudinal axis of the small tube that does not exceed 15% of the length of the small tube and a radial transverse extent that does not exceed 15% of the circumference of the small tube.

11. The ocular implant according to claim 1, wherein a plurality of valves is provided.

12. The ocular implant according to claim 11, wherein a maximum of 4 valves are disposed adjacently in the radial direction, and a maximum of 2 valves are disposed one behind the other in the axial direction.

13. The ocular implant according to claim 10, wherein the valves is disposed at a distance from the first opening equal to between 5% and 35% of the longitudinal extent of the small tube.

14. The ocular implant according to claim 1, wherein the hollow duct comprises a flow limiter formed by an orifice, wherein the orifice comprises an opening the area of which is between 1000 and 3000 $\mu m_2$.

15. The ocular implant according to claim 14, wherein the orifice is disposed at a distance from the first opening corresponding to between 0% and 10% of the longitudinal extent of the small tube.

16. The ocular implant according to claim 1, wherein the at least one pressure-controlled valve is formed such that it opens continuously at a pressure of between 10 mm and 20 mm mercury column.

17. The ocular implant according to claim 1, wherein the diaphragm of the diaphragm valve or the diaphragm of the tongue diaphragm valve comprises at least one opening.

18. The ocular implant according to claim 17, wherein the at least one opening has an area of between 80 and 200 $\mu m_2$.

* * * * *